(12) United States Patent
Hashimoto et al.

(10) Patent No.: US 8,470,846 B2
(45) Date of Patent: Jun. 25, 2013

(54) REMEDY FOR PSYCHONEUROTIC DISEASES

(75) Inventors: Kenji Hashimoto, Chiba (JP); Masaomi Iyo, Chiba (JP); Kaori Koike, Chiba (JP)

(73) Assignee: National University Corporation Chiba University, Chiba (JP)

( * ) Notice: Subject to any disclaimer, the term of this patent is extended or adjusted under 35 U.S.C. 154(b) by 113 days.

(21) Appl. No.: 11/587,621

(22) PCT Filed: Apr. 28, 2005

(86) PCT No.: PCT/JP2005/008123
§ 371 (c)(1),
(2), (4) Date: Oct. 27, 2006

(87) PCT Pub. No.: WO2005/105089
PCT Pub. Date: Nov. 10, 2005

(65) Prior Publication Data
US 2008/0103166 A1    May 1, 2008

(30) Foreign Application Priority Data
Apr. 30, 2004  (JP) ................................ 2004-163826

(51) Int. Cl.
A61K 31/44    (2006.01)
(52) U.S. Cl.
USPC ...................................................... 514/299
(58) Field of Classification Search
None
See application file for complete search history.

(56) References Cited

U.S. PATENT DOCUMENTS

| | | | | |
|---|---|---|---|---|
| 4,695,578 A | * | 9/1987 | Coates et al. | 514/397 |
| 5,185,333 A | | 2/1993 | Kawakita et al. | |
| 5,225,407 A | | 7/1993 | Oakley et al. | |
| 5,962,494 A | * | 10/1999 | Young | 514/397 |
| 2002/0002197 A1 | * | 1/2002 | Mueller et al. | 514/397 |
| 2002/0107244 A1 | | 8/2002 | Howard | |
| 2003/0130266 A1 | * | 7/2003 | Radulovacki et al. | 514/220 |

FOREIGN PATENT DOCUMENTS

| | | |
|---|---|---|
| JP | 05-070456 A | 3/1993 |
| JP | 06-048960 A | 2/1994 |
| WO | WO 03/100091 A | 12/2003 |

OTHER PUBLICATIONS

Costall B and Naylor RJ. The psychopharmacology of 5-HT3 receptors. Pharmacol Toxicol 71(6):401-415, 1992.*
Hagan et al. Interactions between 5-HT3 receptors and cerebral dopamine function: implications for the treatment of schizophrenia and psychoactive substance abuse. Psychopharmacology 112:S68-S75, 1993.*
Weintraub et al, Am J Manag Care. Parkinsons Disease—Part 1: Pathophysiology, symptoms, burden, diagnosis, and assessment. 14:S40-S48, 2008.*
Hague et al. Neurodegenerative disorders: Parkinsons and Huntingtons disease. J Neurol Neurosurg Psychiatry 76(8):1058-1063, 2005.*
Sumiyoshi et al (Am J Psychiatry 158:1722-1725, 2001).*
Giavannini et al (JPET 285:1219-1225, 1998).*
Olincy et al (Biol Psychiatry 47:969-977, 2000).*
Macor et al (Bioorg Med Chem Lett 11:319-321, 2001).*
Koike et al (Schiz Res 76:67-72, 2005).*
Ward et al (Psychiatry Res 64:121-135, 1996).*
Adler et al., "Schizophrenia, Sensor Gating, and Nicotinic Receptors," *Schizophrenia Bulletin* 1998; 24(2): 189-202.
Costall et al., "The Psychopharmacology of 5-HT$_3$ Receptors," *Pharmacology & Toxicology* 1992; 71(6): 401-415.
Freedman et al., "Schizophrenia and Nicotinic Receptors," *Harvard Reviews of Psychiatry* 1994; 2: 179-192.
Freedman et al., "The α7-nicotinic acetylcholine receptor and the pathology of hippocampal interneurous in schizophrenia," *Journal of Chemical Neuroanatomy* 2000; 20: 299-306.
Guan et al., "Decreased protein level of nicotinic receptor α7 subunit in the frontal cortex from schizophrenic brain," *NeuroReport* 1999; 10(8): 1779-1782.
Hashimoto et al., "Amyloid cascade hypothesis of Alzheimer's disease and α7 nicotinic receptor," Review: *Japanese Journal of Neuropsychomarmacology* 2002; 22: 49-53.
Hellström-Lindahl et al., "Expression of nicotinic receptor subunit mRNAs in lymphocytes from normal and patients with Alzheimer's disease," *Alzheimer's Research* 1997; 3(1): 29-36.
Hellström-Lindahl et al., "Regional distribution of nicotinic receptor subunit mRNAs in human brain: comparison between Alzheimer and normal brain," *Molecular Brain Research* 1999; 66: 94-103.
Jones et al., "Nicotinic receptors in the brain: correlating physiology with function," *Trends in Neurosciences* 1999; 22(12): 555-561.
Leonard et al., "Nicbtinic Receptor Function in Schizophrenia," *Schizophrenia Bulletin* 1996; 22(3): 431-445.
Macor et al., "The 5-HT$_3$ Antagonistic Tropisetron (ICS 205-930) is a Potent and Selective α7 Nicotinic Receptor Partial Agonist," *Bioorganic & Medicinal Chemistry Letters* 2001; 11: 319-321.
Pauly et al., "Nicotinic Cholinergic Receptor Deficits in Alzheimer's Disease: Where's the Smoke?" *Alzheimer's Disease Review* 1998; 3:28-34.
Robertson et al., "Zatosetron, a Potent, Selective, and Long-Acting 5HT$_3$ Receptor Antagonist: Synthesis and Structure-Activity Relationships," *J. Med. Chem.* 1992; 35(2): 310-319.
Schröder et al., "Nicotinic'Acetylcholine Receptors in Alzheimer's disease," *Alzheimer's Disease Review* 1998; 3: 20-27.
Shimohama et al., "Changes in Nicotinic and Muscarinic Cholinergic Receptors in Alzheimer-Type Dementia," *Journal of Neurochemistry* 1986; 46(1): 288-293.
Hagan, R.M. et al., "Interactions between 5-HT$_3$ receptors and cerebral dopamine function: implications for the treatment of schizophrenia and psychoactive substance abuse," *Psychopharmacology* 1993; 112(1 Suppl): S68-S75.

(Continued)

*Primary Examiner* — Craig Ricci
(74) *Attorney, Agent, or Firm* — Wolf, Greenfield & Sacks, P.C.

(57) ABSTRACT

A medicinal preparation for preventing and/or treating psychoneurotic diseases such as integration dysfunction and Alzheimer's disease which contains tropisetron or its pharmaceutically acceptable salt as the active ingredient.

4 Claims, 1 Drawing Sheet

OTHER PUBLICATIONS

Koike, K. et al., "Tropisetron improves deficits in auditory P50 suppression in schizophrenia," *Schizophrenia Research* Jul. 1, 2005; 76(1): 67-72.

Rzewuska, M. et al., "Tropisetron as an adjunct drug in treatment of chronic, drug resistant schizophrenia—negative results," *New Trends in Experimental and Clinical Psychiatry* 2000; 16(1-4): 7-10.

Macor, I.E. et al., "The 5-HT3 Antagonist Tropisetron (ICS 205-930) is a Potent and Selective α7 Nicotinic Receptor Partial Agonist," *Bioorganic & Medicinal Chemistry Letters* 2001; 11:319-321.

Hashimoto, K. et al., "Phencyclidine-induced cognitive deficits in mice are improved by subsequent subchronic administration of tropisetron: Role of α7 nicotinic receptors," *European Journal of Pharmacology* 2006; 553:191-195.

Shina, A. et al., "A randomized, double-blind, placebo-controlled trial of tropisetron in patients with schizophrenia," *Annals of General Psychiatry* 2010; 9:27.

* cited by examiner

Effects of tropisetron on abnormalities in P50 auditory evoked potential in schizophrenic patients.
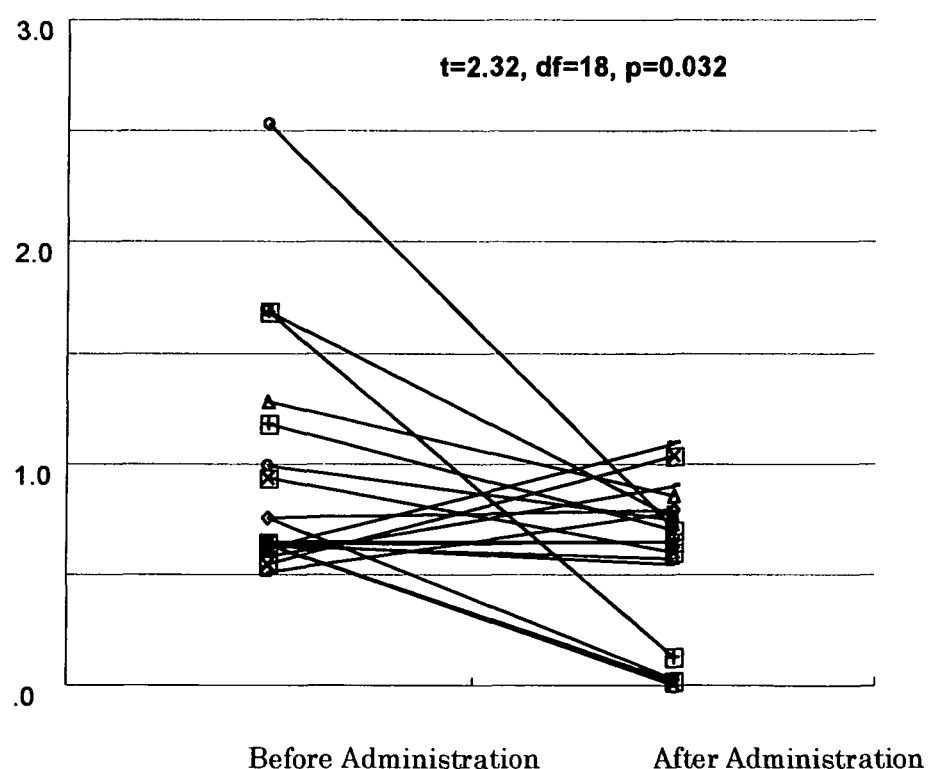

REMEDY FOR PSYCHONEUROTIC DISEASES

RELATED APPLICATIONS

This application is a national stage filing under 35 U.S.C. §371 of PCT International application PCT/JP2005/008123, filed Apr. 28, 2005.

TECHNICAL FIELD

The invention relates to a medicament for preventing and/or treating psychoneurotic disorders. More specifically, the invention relates to an agent for psychoneurotic disorders, containing tropisetron ((1R,3r,5S)-8-methyl-8-azabicyclo[3.2.1]oct-3-yl 1H-indole-3-carboxylate) or its pharmaceutically acceptable salt.

BACKGROUND ART

Accompanying with changes in social lifestyle and aging of society, the overall number of patients with psychoneurotic disorders tends to increase. For example, at present the number of patients with Alzheimer's disease, which is known as a representative neurodegenerative disease, is estimated to be 1.5 million in Japan and 4.0 million in the U.S. According to a prediction, this number increases with an increase in aged people in countries centering around developed countries, and in 25 years, approximately 22 million people throughout the world will suffer from this disease. Currently, in the cognitive dysfunction of Alzheimer's disease (so-called dementia), the involvement of dysfunction of the acetylcholinergic nervous system in the brain has been clarified on the basis of many neuropathological findings, and therefore an inhibitor of acetylcholine degrading enzyme (cholinesterase inhibitor) is clinically used. However, it is hard to say that the inhibitor is sufficiently therapeutically effective. Practically, there is almost no effective method for the prevention and treatment of the disease.

On the other hand, schizophrenia occurs in approximately 1% of the population regardless of race and geographic area, and this is a psychoneurotic disorder, the onset of which often occurs in young generations from adolescence to the age of 20-29. The number of hospital patients with schizophrenia in Japan accounts for approximately 15% of the total number of hospital beds, resulting in a significant problem in terms of medical cost. As symptoms of schizophrenia, there are positive symptoms such as hallucination and delusion, negative symptoms such as flat or blunted emotion, lack of motivation and social withdrawal, as well as cognitive dysfunction. Among these symptoms, cognitive dysfunction may possibly be a core symptom of schizophrenia, and is considered to deteriorate the quality of life (QOL) of patients. Pharmacological therapy is essential for the treatment of schizophrenia, and pharmaceutical agents such as phenothiazine compounds, butyrophenone compounds, benzamide compounds, iminodibenzyl compounds, thiepine compounds, indole compounds and serotonin-dopamine receptor blockers are administered. However, although these pharmaceutical agents actually used in clinical sites are effective for positive symptoms such as hallucination and delusion, they show almost no effect on cognitive dysfunction. Thus, the development of therapeutic agents for cognitive dysfunction has been awaited in Japan and abroad.

Meanwhile, acetylcholine is one of the major neurotransmitters of the central nervous system, and is known to play an important role in the regulation of nervous activities in the cerebral cortex and hippocampus. In recent years, it is speculated that $\alpha 7$ subtype of nicotinic receptor ($\alpha 7$ nicotinic receptor) is involved in the pathological conditions of psychoneurotic diseases such as schizophrenia and Alzheimer's disease.

For example, in the brain (cerebral cortex and hippocampus, etc.) of a schizophrenic patient at autopsy, a decrease in the number of $\alpha 7$ nicotinic receptors has been reported. It is also reported that an abnormality in P50 auditory evoked potential observed in schizophrenic patients is improved by the administration of nicotine, and that $\alpha 7$ nicotinic receptors are involved in this phenomenon (refer to Non-patent documents 1-6).

Similarly, in the cerebral cortex and hippocampus of patients with Alzheimer's disease at autopsy, a decrease in the number of nicotinic receptors ($\alpha 4 \beta 2$ nicotinic receptors and $\alpha 7$ nicotinic receptors) has been reported (refer to Non-patent documents 7-9). In addition, it is reported that the amount of $\alpha 7$ nicotinic receptor mRNA of the lymphocytes in Alzheimer's patients is significantly higher than that in normal subjects (refer to Non-patent document 10). It is also reported that the amount of $\alpha 7$ nicotinic receptor mRNA in the hippocampus of Alzheimer's patients is significantly higher than that in normal subjects (refer to Non-patent document 11). In this report, no difference in the amount of mRNA in other subtypes ($\alpha 3$ and $\alpha 4$) was observed between the brain of Alzheimer's patients and the brain of normal subjects, suggesting that $\alpha 7$ nicotinic receptors play an important role in the pathological condition of Alzheimer's disease (refer to Non-patent document 12).

As described above, $\alpha 7$ nicotinic receptors in the brain have been speculated to play an important role in psychoneurotic disorders such as schizophrenia and Alzheimer's disease. However, although several compounds including tropisetron and GTS-21 which affect $\alpha 7$ nicotinic receptors are known at present (refer to Non-patent document 13), no pharmaceutical agent that has improving effects on these psychoneurotic disorders, and also has pharmacokinetic features of resistance to administration to humans as well as safety, has been reported; in addition, in the above-mentioned non-patent document 13, no specific action of tropisetron on psychoneurotic disorders such as schizophrenia and Alzheimer's disease, in particular on cognitive dysfunction, has been described. Furthermore, with respect to tropisetron, this is originally used as an antiemetic agent having an antagonistic action against serotonin 5-$HT_3$ receptor, and this kind of pharmaceutical agent is not known to be used for the prevention and treatment of psychoneurotic disorders. Thus, a pharmaceutical agent effective to humans to such an extent that it can be actually used for the prevention and treatment of psychoneurotic disorders such as schizophrenia and Alzheimer's disease, and in particular psychoneurotic disorders with cognitive dysfunction, has not yet been known to date.

[Non-patent document 1] Freedman R, Adler L E, Bickford P, Byerley W, Coon H, Cullum C M, Griffith J M, Harris J G, Leonard S, Miller C, et al. Schizophrenia and nicotinic receptors. Harvard Reviews of Psychiatry, 2:179-192, 1994.

[Non-patent document 2] Leonard S, Adams C, Breese C R, Adler L E, Bickford P, Byerley W, Coon H, Griffith J M, Miller C, Myles-Worsley M, Nagamoto H T, Rollins Y, Stevens K E, Waldo M, Freedman R. Nicotinic receptor function in schizophrenia. Schizophrenia Bulletin, 22:431-445, 1996.

[Non-patent document 3] Adler L E, Olincy A, Waldo M, Harris J G, Griffith J, Stevens K, Flach K, Nagamoto H, Bickford P, Leonard S, Freedman R. Schizophrenia, sensory gating, and nicotinic receptors. Schizophrenia Bulletin, 24:189-202, 1998.

[Non-patent document 4] Jones S, Sudweeks S, Yakel J L. Nicotinic receptors in the brain: correlating physiology with function. Trends in Neurosciences, 22:555-561, 1999.

[Non-patent document 5] Freedman R, Adams C E, Leonard S. The alpha7-nicotinic acetylcholine receptor and the pathology of hippocampal interneurons in schizophrenia. J Chem Neuroanat 20: 299-306, 2000.

[Non-patent document 6] NeuroReport, 10:1779-1782, 1999.

[Non-patent document 7] Journal of Neurochemistry, 46:288-293, 1986.

[Non-patent document 8] Alzheimer's Disease Reviews, 3:20-27, 1998.

[Non-patent document 9] Alzheimer's Disease Reviews, 3:28-34, 1998.

[Non-patent document 10] Alzheimer's Research, 3:29-36, 1997

[Non-patent document 11] Molecular Brain Research, 66:94-103, 1999.

[Non-patent document 12] Review: Japanese Journal of Neuropsychopharmacology 22: 49-53, 2002.

[Non-patent document 13] Macor J. E. et al., Bioorganic & Medicinal Chemistry Letters, 11, 319-321, 2001.

DISCLOSURE OF THE INVENTION

Problem to be Solved by the Invention

Therefore, the development of preventive drugs and therapeutic drugs for psychoneurotic disorders such as schizophrenia and Alzheimer's disease, in particular for cognitive dysfunction, has been desired. The object of the present invention is to provide a medicinal preparation effective for such psychoneurotic disorders.

Means of Solving the Problem

Inventors of the invention devoted themselves to the research to solve the above problem, and found for the first time that an abnormality in P50 auditory evoked potential, which is one of the parameters of cognitive dysfunction, observed in schizophrenic patients is improved by the administration of tropisetron ((1R,3r,5S)-8-methyl-8-azabicyclo[3.2.1]oct-3-yl 1H-indole-3-carboxylate) that has an antagonistic action against serotonin 5-$HT_3$ receptor and a partial agonistic action on α7 nicotinic receptor, and completed this invention.

Namely, the invention relates to an agent for psychoneurotic disorders, containing tropisetron or its pharmaceutically acceptable salt.

The invention also relates to said agent for psychoneurotic disorders, wherein the psychoneurotic disorder is a psychoneurotic disorder associated with acetylcholinergic nerves.

The invention also relates to the above agent for psychoneurotic disorders, wherein the psychoneurotic disorder is a psychoneurotic disorder which exhibits one or more of symptoms selected from the group consisting of cognitive dysfunction, attentional deficit disorder, depression, anxiety, epilepsy and pain.

The invention also relates to the above agent for psychoneurotic disorders, wherein the psychoneurotic disorder is at least one of the disorders selected from the group consisting of schizophrenia, Alzheimer's disease, Parkinson's disease, Huntington's disease and Tourette's syndrome.

The invention also relates to the above agent for psychoneurotic disorders, wherein the agent is used for the treatment of cognitive dysfunction in schizophrenia.

Effects of the Invention

Since tropisetron or its pharmaceutically acceptable salt induces activation of acetylcholinergic nerves in the brain due to its antagonistic action against serotonin 5-$HT_3$ receptor and stimulatory action on α7 nicotinic receptor, an agent for psychoneurotic disorders of the invention containing tropisetron or its pharmaceutically acceptable salt exhibits effects on various psychoneurotic disorders, and is effective for their prevention and/or treatment. For example, the agent is effective in the prevention and/or treatment of psychoneurotic disorders involving abnormalities in acetylcholinergic nerves, specifically, such as schizophrenia, Alzheimer's disease, Tourette's syndrome, Parkinson's disease, Huntington's disease as well as various psychoneurotic disorders exhibiting symptoms such as cognitive dysfunction, attentional deficit disorder, anxiety, depression, epilepsy and pain.

BRIEF DESCRIPTION OF THE DRAWINGS

FIG. 1 shows effects of tropisetron on abnormalities in P50 auditory evoked potential observed in schizophrenic patients.

BEST EMBODIMENTS FOR CARRYING OUT THE INVENTION

First, meaning or definition of terms used herein is described. In the present invention, psychoneurotic disorders refer to a concept encompassing various psychiatric disorders such as schizophrenia and depression, various neurodegenerative disorders such as Alzheimer's disease, Parkinson's disease and Huntington's disease, and neurological disorders such as Tourette's syndrome.

In the present invention, schizophrenia refers to a chronic neurological disorder, the onset of which occurs mainly in early and middle adolescence, which has root symptoms of disturbance of ego and thinking disorder, and which progresses gradually while repeating positive symptoms such as hallucination and delusion. In the present invention, Alzheimer's disease refers to a chronic neurodegenerative disorder, the onset of which occurs generally at the age of 60 or older, which is called senile dementia, and which progresses gradually with a central symptom of cognitive dysfunction.

The agent for psychoneurotic disorders containing tropisetron or its pharmaceutically acceptable salt of the invention can be administered orally or parenterally. For oral administration, well-known forms of administration such as tablets, capsules, coated tablets, lozenges, and liquid preparations including solutions and suspensions can be used. For parenteral administration, rectal administration using suppositories, transdermal administration using patches, liniments and gel, transmucosal administration using sprays and aerosols may be performed, and the administration may also be performed by intravenous, intramuscular, subcutaneous or intraventricular injection.

In the agent for psychoneurotic disorders of the invention, tropisetron can be used as both forms of free base and its pharmaceutically acceptable salt. As pharmaceutically acceptable salts, pharmaceutically acceptable acid addition salts are preferred, and in particular, hydrochloride salt is preferred.

The agent for psychoneurotic disorders of the invention can contain other medicinal components in addition to tropisetron or its pharmaceutically acceptable salt. Furthermore, in addition to these medicinal components, physiologically-acceptable appropriate substances well known to those skilled in the art can be contained, which include, without limitation, antioxidants, stabilizers, preservatives, flavoring agents, coloring agents, solubilizing agents, solubilizers, surfactants, emulsifiers, antifoaming agents, viscosity modifiers, gelatinizing agents, absorption promoters, dispersants, excipients, pH modifiers and others.

Thus, the agent for psychoneurotic disorders of the invention can be prepared by appropriately blending tropisetron or its pharmaceutically acceptable salt with the above-mentioned substances. When the agent for psychoneurotic disorders of the invention is prepared as an injection preparation (for subcutaneous, intramuscular, or intravenous injection), a form of solution or suspension is particularly preferred; when it is prepared for vaginal or rectal administration, a form of semi-solid agent such as creams or suppositories is particularly preferred; when it is prepared for transnasal administration, a form of powder, nose drop, or aerosol is particularly preferred. Any of these preparations can be prepared in accordance with any method of pharmaceutical technology well-known to those skilled in the art, such as those described in Remington's Pharmaceutical Sciences (Mack Publishing Co., Easton, Pa., 1970). In the injection preparations, for example, blood-plasma-derived proteins such as albumin, amino acids such as glycine, and sugars such as mannitol can be added; in addition, buffering agents, solubilizing agents, isotonic agents and others can be added. For use as aqueous preparations or lyophilized agents, preferably a surfactant such as Tween® 80 or Tween® 20 is added to prevent coagulation. Parenteral formulations other than injection preparations may contain distilled water or saline, polyalkylene glycol such as polyethylene glycol, vegetable derived oil, hydrogenated naphthalene and others. Preparations for vaginal or rectal administration such as suppositories contain, for example, polyalkylene glycol, petroleum jelly, cacao oil, etc., as a general excipient. Preparations for vaginal administration may contain absorption promoters such as bile salt, ethylenediamine salt, citrate and others. Preparations for inhalation may be a solid, and may contain, for example lactose as an excipient; preparations for nose drop may be water or oily solution.

The accurate dose and regimen of the agent for psychoneurotic disorders of the invention are adjusted depending on factors such as the amount required, therapeutic method, type of disease and degree of necessity of each subject to be treated. Specifically, the dose can be determined depending on the age, body weight, general state of health, sex, diet, the time and route of administration, excretion rate, combination of pharmaceutical agent, and disease state of a patient; other factors can be taken into consideration as well. Tropisetron or its pharmaceutically acceptable salt does not show pharmacokinetic problems in humans, and can be used safely. Its daily dose differs depending on the state and body weight of a patient, the kind of compound and the administration route. However, it is desirable that for parenteral administration, the agent is administered subcutaneously, intravenously, intramuscularly or rectally at a dose of approximately 0.01-100 mg/person/day as a tropisetron (free base), preferably at 0.1-50 mg/person/day; and for oral administration, the agent is administered at a dose of approximately 0.01-500 mg/person/day, preferably at 0.1-100 mg/person/day.

EXAMPLES

The invention is described more specifically with reference to examples below, but the invention should not be limited to these examples. In addition, various modifications can be made within the range of the technical idea of the invention.

Example 1

(1) Subject

Twenty-two patients with schizophrenia (14 males and 8 females, average age: 39.8 years old (standard deviation 14.0), age range: 18-60 years old) were selected as subjects. The subjects were diagnosed by psychiatrists on the basis of DSM-IV criteria. Psychiatric symptoms and cognitive functions of the subjects were evaluated using Brief Psychiatric Rating Scale (BPRS), Global Assessment of Functioning (GAF), Mini-Mental State Examination (MMSE) and Wechsler Adult Intelligence Scale-Revised (WAIS-R).

(2) Experimental Method

First, a baseline P50 auditory evoked potential of a subject was measured (conditioning P50), then the P50 was measured 1 h after administration of 10 mg of tropisetron (test P50). P50 is a positive brain wave which appears approximately 50 m seconds after an auditory stimulus. Consecutive click sounds with an interval of 500 m seconds (conditioning stimulus and test stimulus) at 70 dB were presented every 10 seconds for 120 times, and the brain wave measured at the parietal region was summed to identify P50. The resistance of an electrode was set at 10 kW or less, and the brain wave exceeding ±70 mV was omitted as artifact. The largest positive wave between 40 ms and 90 ms after the conditioning stimulus was designated to be the conditioning P50, and the positive wave after the test stimulus whose latency is the closest to that of the conditioning P50 was designated to be the test P50. The amplitude of P50 was defined as the difference between the positive peak and the preceding negative trough. The P50 ratio was defined as the amplitude of the test P50 divided by the amplitude of the conditioning P50.

(3) Statistical Analysis

Data were expressed as average±standard deviation. The statistical analysis between two groups was performed using Student's t-test. The relationship between variables was confirmed by Pearson's product-moment correlation coefficient. p Values of 0.05 or less were designated to be statistically significant.

(4) Results

Results of the baseline P50 from 22 subjects were analyzed. The amplitudes of the conditioning P50 and test P50 were 2.59±1.45 and 1.76±1.00, respectively, and their latencies were 59.64±13.03 and 57.18±16.15, respectively. The P50 ratio was 0.84±0.55. The baseline P50 ratios of three subjects (13.6%) were 0.5 or less (0.07, 0.25, 0.28). Table 1 shows average values of data from 19 subjects in whom baseline P50 ratio was larger than 0.5. While no significant differences in both the amplitude and latency of conditioning P50 were observed between before and after the administration of tropisetron (t=0.79, df=18, p=0.44; t=1.05, df=18, p=0.31), there was a significant decrease in the P50 ratio between before and after the administration of tropisetron (t=2.32, df=18, p=0.033). FIG. 1 shows P50 ratios before and after the administration of tropisetron in 19 subjects. In four subjects, the P50 ratio improved to 0.5 or less.

As shown in the above results, P50 ratios significantly decreased by the administration of tropisetron in patients with schizophrenia and thus it is understood that tropisetron improves cognitive dysfunction in schizophrenia. Accordingly, the agent for psychoneurotic disorders containing tropisetron or its pharmaceutically acceptable salt was shown to be effective as a preventive drug and/or therapeutic drug for psychoneurotic disorders including schizophrenia and those exhibiting cognitive dysfunction.

TABLE 1

Effects of tropisetron on abnormalities in P50 auditory evoked potential in schizophrenic patients.

| P50 Characteristic | Before | | After | |
|---|---|---|---|---|
| | Mean | SD | Mean | SD |
| Amplitute (mV) | | | | |
| conditioning | 2.40 | 1.31 | 2.65 | 1.47 |
| test | 1.93 | 0.96 | 1.45 | 1.24 |
| Latency (msec) | | | | |
| conditioning | 58.21 | 12.61 | 59.79 | 13.41 |
| test | 55.79 | 15.98 | 59.16 | 14.02 |
| P50(T/C)ratio | 0.94 | 0.53 | 0.61* | 0.33 |

*Significant between-group difference (t = 2.32, df = 18, p = 0.032)

INDUSTRIAL APPLICABILITY

As explained above, the agent for psychoneurotic disorders of the invention can be used as an effective medicament for various psychoneurotic disorders including schizophrenia and Alzheimer's disease, in particular cognitive dysfunction for which no effective pharmaceutical agents exist to date.

The invention claimed is:

1. A method for treating abnormality in P50 auditory evoked potential of cognitive dysfunction in schizophrenia, comprising:
   (a) measuring a baseline P50 auditory evoked potential ratio of a subject,
   (b) administering to the subject whose baseline P50 auditory evoked potential ratio is larger than 0.5 an agent containing tropisetron or its pharmaceutically acceptable salt at a dose of tropeistron free base of at least 10 mg/day, and
   (c) measuring P50 auditory evoked potential ratio of the subject, wherein it is determined that the cognitive dysfunction is improved if the P50 auditory evoked potential ratio is 0.5 or less.

2. The method according to claim 1, wherein the agent containing tropisetron or its pharmaceutically acceptable salt is administered orally at a dose of tropisetron free base of 10-500 mg/day.

3. The method according to claim 2, wherein the agent containing tropisetron or its pharmaceutically acceptable salt is administered orally at a dose of tropisetron free base of 10-500 mg/day.

4. The method according to claim 3, wherein the agent containing tropisetron or its pharmaceutically acceptable salt is administered orally at a dose of tropisetron free base of 10 mg/day.

* * * * *

UNITED STATES PATENT AND TRADEMARK OFFICE
CERTIFICATE OF CORRECTION

| | | |
|---|---|---|
| PATENT NO. | : 8,470,846 B2 | Page 1 of 1 |
| APPLICATION NO. | : 11/587621 | |
| DATED | : June 25, 2013 | |
| INVENTOR(S) | : Kenji Hashimoto et al. | |

It is certified that error appears in the above-identified patent and that said Letters Patent is hereby corrected as shown below:

In the Claims:

Claim 3, column 8, at line 20, should read:

3. The method according to claim 2, wherein the agent containing tropisetron or its pharmaceutically acceptable salt is administered orally at a dose of tropisetron free base of 10-100 mg/day.

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,470,846 B2
APPLICATION NO.  : 11/587621
DATED             : June 25, 2013
INVENTOR(S)      : Hashimoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 139 days.

Signed and Sealed this
Eighth Day of September, 2015

Michelle K. Lee
*Director of the United States Patent and Trademark Office*